(12) United States Patent
Ponticiello et al.

(10) Patent No.: US 9,427,335 B2
(45) Date of Patent: Aug. 30, 2016

(54) METHOD FOR RINSING AND DELIVERING BONE GRAFT

(71) Applicant: Biomet Biologics, LLC, Warsaw, IN (US)

(72) Inventors: Michael Ponticiello, Mission Viejo, CA (US); Surinder Saran Mathur, Irvine, CA (US)

(73) Assignee: Biomet Biologics, LLC., Warsaw, IN (US)

( * ) Notice: Subject to any disclaimer, the term of this patent is extended or adjusted under 35 U.S.C. 154(b) by 294 days.

(21) Appl. No.: 14/218,013

(22) Filed: Mar. 18, 2014

(65) Prior Publication Data

US 2015/0265423 A1    Sep. 24, 2015

(51) Int. Cl.
*A61F 2/46* (2006.01)
*A61F 2/28* (2006.01)
*A61B 17/88* (2006.01)

(52) U.S. Cl.
CPC .......... *A61F 2/4644* (2013.01); *A61B 17/8825* (2013.01); *A61F 2/28* (2013.01); *A61F 2/4601* (2013.01); *A61F 2002/2835* (2013.01)

(58) Field of Classification Search
CPC .......... A61F 2/46; A61F 2/28; A61F 2/4644; A61F 2/4601
See application file for complete search history.

(56) References Cited

U.S. PATENT DOCUMENTS

| | | | |
|---|---|---|---|
| 1,363,128 A | 12/1920 | Kitaoaka | |
| 3,493,503 A | 2/1970 | Mass | |
| 4,366,822 A | 1/1983 | Altshuler | |
| 4,751,921 A | 6/1988 | Park | |
| 6,554,803 B1 * | 4/2003 | Ashman | A61M 37/00 433/89 |
| 6,595,979 B1 | 7/2003 | Epstein et al. | |
| 7,819,846 B2 | 10/2010 | Lee | |
| 2002/0049405 A1 * | 4/2002 | Deslauriers | A61B 17/8827 604/82 |
| 2003/0069543 A1 | 4/2003 | Carpenter et al. | |
| 2005/0013872 A1 | 1/2005 | Freyman | |
| 2010/0172863 A1 | 7/2010 | Wasielewski | |
| 2011/0160857 A1 * | 6/2011 | Bracone | A61F 2/2875 623/16.11 |

FOREIGN PATENT DOCUMENTS

WO    WO-2015142891 A1    9/2015

OTHER PUBLICATIONS

"International Application Serial No. PCT/US2015/021021, International Search Report mailed Sep. 10, 2015", 5 pgs.
"International Application Serial No. PCT/US2015/021021, Written Opinion mailed Sep. 10, 2015", 7 pgs.

* cited by examiner

*Primary Examiner* — Christopher Beccia
(74) *Attorney, Agent, or Firm* — Schwegman Lundberg & Woessner, P.A.

(57) ABSTRACT

A method for rinsing and delivering a bone graft. The method includes selecting a delivery syringe containing bone graft material wherein the syringe is coupled to a filter assembly, determining a bone graft:fluid ratio, washing the bone graft material, reconstituting the bone graft material to generate the bone graft with the predetermined bone graft:fluid ratio, and delivering the bone graft to a surgical site.

20 Claims, 4 Drawing Sheets

METHOD FOR RINSING AND DELIVERING BONE GRAFT

BACKGROUND

This section provides background information related to the present disclosure which is not necessarily prior art.

Bone grafts are commonly used in surgical procedures to replace missing bone, to repair bone fractures, and to fuse bone, such as during spinal fusions. Bone grafts may be autologous, but many allografts of bone material isolated from cadavers and obtained from a bone bank. Allograft tissue, which contains viable cells, must be stored frozen in a cryopreservative solution. The liquid cryopreservative must be thoroughly rinsed and removed from the tissue prior to transplantation. Typically, the graft material is contained in a vial, and must be carefully rinsed. The graft material is typically granular in nature and the rinsing process often leads to loss of material because the rinsing process is typically performed several times, and is cumbersome to perform. Additionally, the rinsing process involves physical contact with the graft material, which increases the risk of contamination.

Open bore graft delivery syringes are common in orthopedic applications. Open bore delivery syringes currently on the marked are sealed with either a flat end cap, or a luer or nozzle-type cap for adding additional fluid. To achieve the desired handling characteristics of any hydrated bone graft (autograft, allograft, synthetic, xenograft), it may be necessary to adjust the graft-to-fluid ratio, by removing some of the fluid while retaining the graft. Using existing delivery syringes would not address this issue because the granular graft material would clog the luer/nozzle fitting, preventing any liquid, such as cryopreservative, from being removed.

A more efficient means for thoroughly washing graft material that would also minimize tissue loss during transfer while not compromising graft sterility is needed.

SUMMARY

This section provides a general summary of the disclosure, and is not a comprehensive disclosure of its full scope or all of its features.

A bone graft delivery syringe with a filter cap assembly is disclosed. The bone graft delivery syringe comprises a transparent tubular body with distal and proximal ends. The tubular body defines an inner and outer surface, and an internal space. The tubular body may further comprise evenly spaced volumetric markings. The distal end of the tubular body comprises a coupling feature and an open bore. The proximal end of the tubular body comprises flanges. A plunger is inserted through the proximal end. Bone graft material, comprising bone particles, can be stored within the internal space of the delivery syringe. The filter cap comprises a nozzle opening and a filter. The filter has a surface area that is substantially larger than that of the nozzle opening, and only slightly smaller than that of the open bore. The effective pore size of the filter is smaller than the bone particle stored within the delivery syringe. Only bone particles of negligible size, such as bone dust or bone powder, can flow through the filter. The filter cap is removably coupled to the coupling feature at the distal end of the tubular body. For example, the filter cap can be removably coupled to the tubular body by threading, luer fittings, bayonet slots, an interference fit, or by any other means generally available in the art. The filter is placed in line with the open bore, in between the nozzle opening and the bone graft material stored within the delivery syringe.

A method for rinsing and delivering a bone graft is also disclosed. The method comprises selecting a syringe containing bone graft material and a cryopreservative solution, the syringe comprising a proximal plunger, a distal open bore, and a filter removably coupled to the syringe adjacent to the distal open bore; determining a bone graft:fluid ratio; depressing the plunger to expel the cryopreservative solution from the syringe and through the filter, wherein the bone graft material is maintained within the syringe; inserting a distil end of the syringe into a receptacle containing a wash fluid and drawing the plunger to aspirate the wash solution into the syringe; inverting the syringe to mix the wash solution with the bone graft material; depressing the plunger to expel the wash solution; reconstituting the graft material by inserting the distil end of the syringe into a second receptacle containing a reconstitution fluid and drawing the plunger to aspirate the reconstitution fluid to obtain the predetermined bone graft:fluid ratio; inverting the delivery syringe to generate a bone graft; and decoupling the filter from the syringe and delivering the bone graft through the open bore to a surgical site by depressing the plunger. The wash solution is saline or phosphate buffered saline (PBS) and the reconstitution fluid is saline, PBS, whole blood, a blood fraction, bone marrow aspirate, concentrated bone marrow aspirate or combinations thereof.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Example embodiments will now be described more fully with reference to the accompanying drawings.

The present technology generally provides devices and methods for rinsing and delivering bone graft material to a surgical site. Bone graft material can be stored in a cryopreservative within a bone graft delivery syringe coupled to a filter assembly. The delivery syringe containing the bone graft material and coupled to the syringe assembly can be stored, for example, at −80° C. The present devices and methods provide an efficient, easy-to-use, self-contained system that allows the user to (1) thoroughly wash away liquid cryopreservative solution from the bone graft material (2) adjust the graft-to-fluid ratio to achieve the desired handling characteristics, (3) minimize graft loss throughout the process, (4) minimize the risk for contamination, and (5) easily deliver the washed graft to the surgical site.

Figure 1:
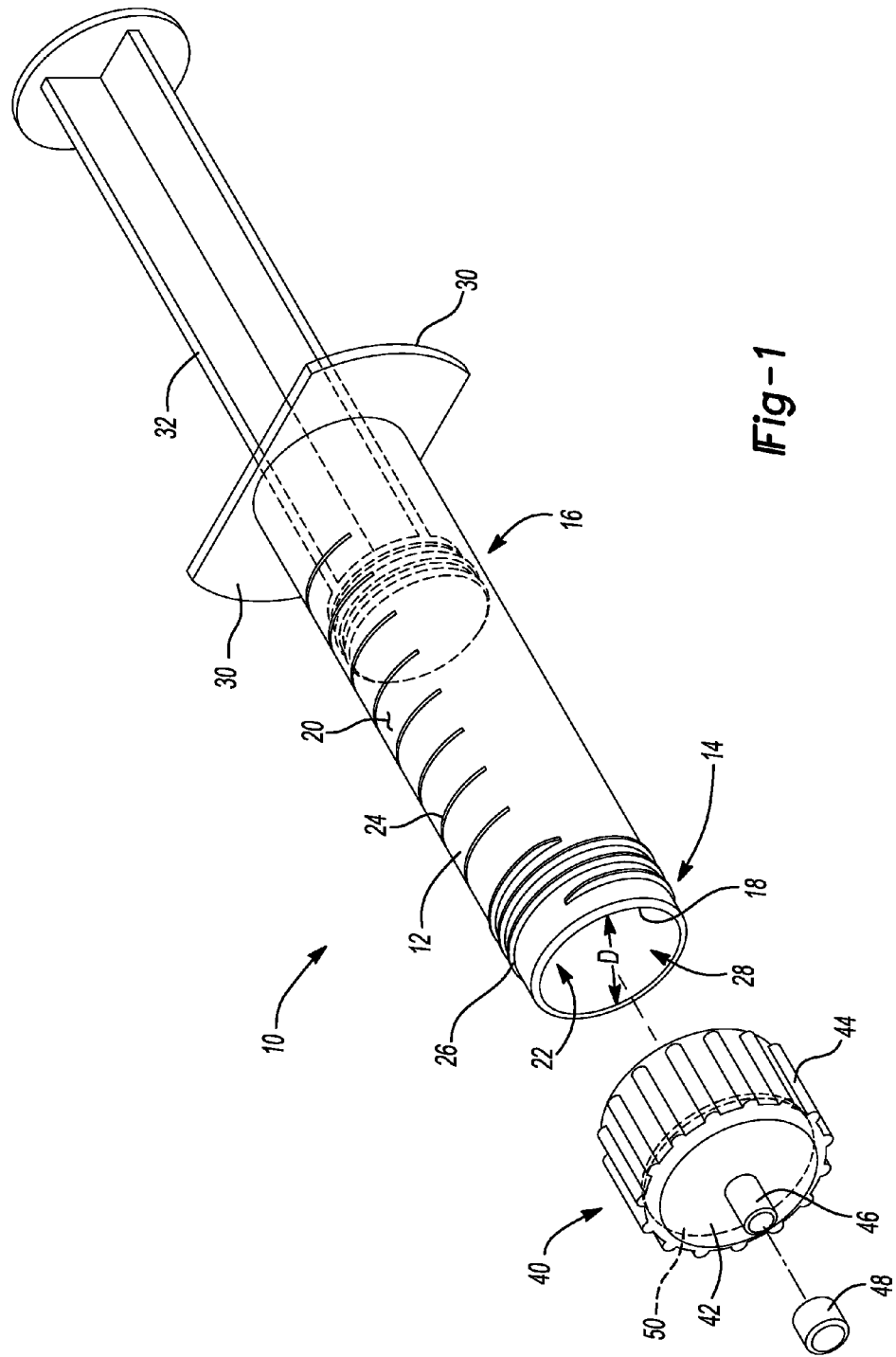
FIG. 1 is a diagrammatic illustration of a delivery syringe and a filter assembly for rinsing and delivering a bone graft.

With reference to FIG. 1, the present teachings provide a bone graft delivery syringe 10. The delivery syringe 10 comprises a transparent tubular body 12 with a distal end 14 and a proximal end 16. The tubular body 12 has an inner surface 18, and an outer surface 20, that define an internal space 22. In some embodiments, the tubular body 12 may further comprise evenly spaced volumetric markings 24. When present, the volumetric markings 24 can refer to a specific internal volume, for example, in mL or cc, or the markings 24 can refer to a non-specific volume. Whether referring to specific or non-specific volumes, the volumetric markings 24 are evenly spaced so that relative volumes can be determined. The distal end 14 of the tubular body 12 comprises a coupling feature, such as threading 26, on the outer surface 20 and an open bore 28. The open bore 28 has a diameter "D" that is substantially similar to the diameter of the internal space 22 defined by the tubular body 12. The proximal end 16 of the tubular body 12 comprises flanges 30. A plunger 32 is inserted through the proximal end 16.

Figure 2:
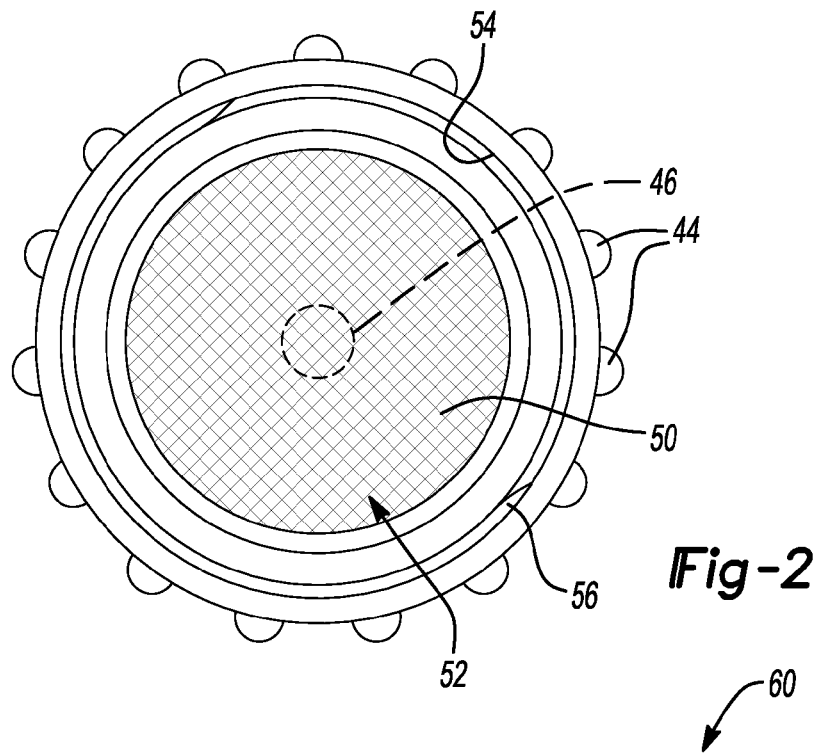
FIG. 2 is a representation of a filter assembly comprising a nozzle and a filter.

A filter assembly 40 is removably coupled to the delivery syringe 10 by means generally available in the art. The filter assembly 40 comprises an outer surface 42, gripping protrusions 44, a nozzle opening 46, a detachable nozzle cap 48, and a filter 50. As shown in FIG. 2, the filter assembly 40 defines an internal compartment 52 having an inner surface 54. As mentioned above, the filter assembly 40 is removably coupled to the delivery syringe 10. As non-limiting examples, the filter assembly 40 can be removably coupled to the delivery syringe 10 by threading, luer fittings, bayonet slots, an interference fit, or by any other means generally available in the art. In FIG. 1, the inner surface 54 comprises threading 56, which enables the filter assembly 40 to be threadedly coupled to the delivery syringe 10. The filter 50 has a surface area that is substantially larger than that of the nozzle opening 46, and only slightly smaller than that of the open bore 28. The filter 50 has a sufficient surface area to wash and reconstitute the bone particles, while preventing substantial bone particle loss. The effective pore size of the filter 50 is smaller than the bone particles that may be stored within the delivery syringe 10. In some embodiments, only bone particles of negligible size, such as bone dust or bone powder, can flow through the filter 50. In other embodiments, the effective pore size for the filter 50 is smaller than the smallest bone particle stored within the delivery syringe 10, so that wash solution or reconstitution solution can pass through the filter 50, but not bone powder or bone dust. When the filter assembly 40 is coupled to the delivery syringe 10, the filter 50 is placed in line with the open bore 28, in between the nozzle opening 46 and any bone graft material stored within the delivery syringe 10.

Figure 3:
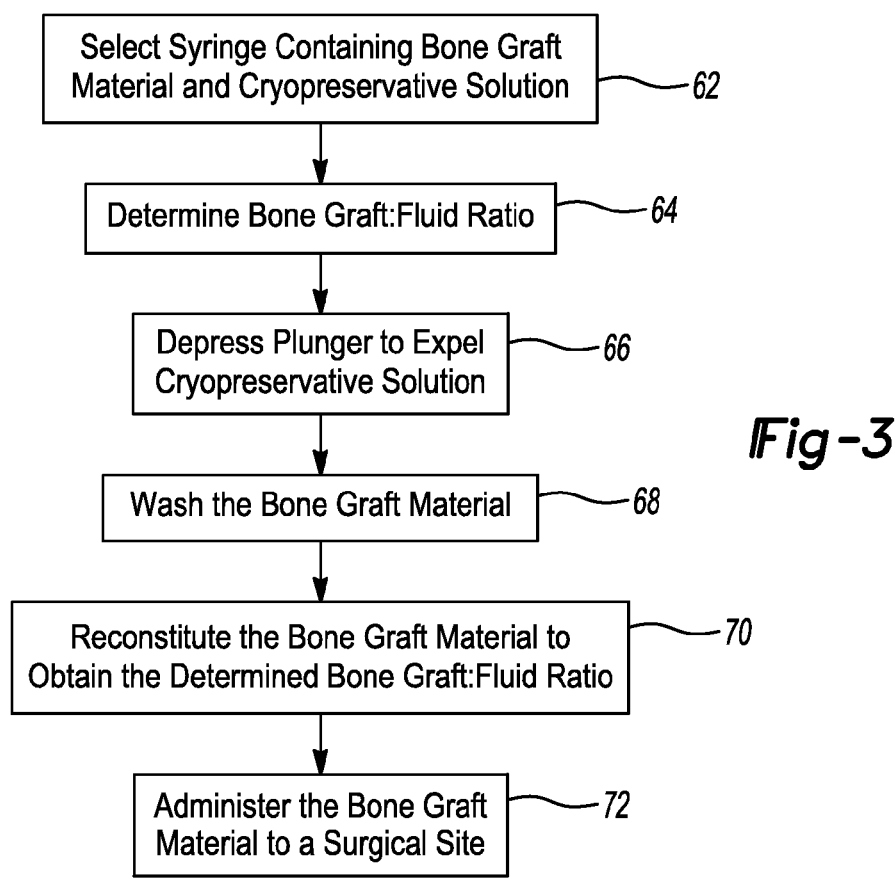
FIG. 3 is a diagrammatic illustration of a method of rinsing and delivering a bone graft.
Figure 4:
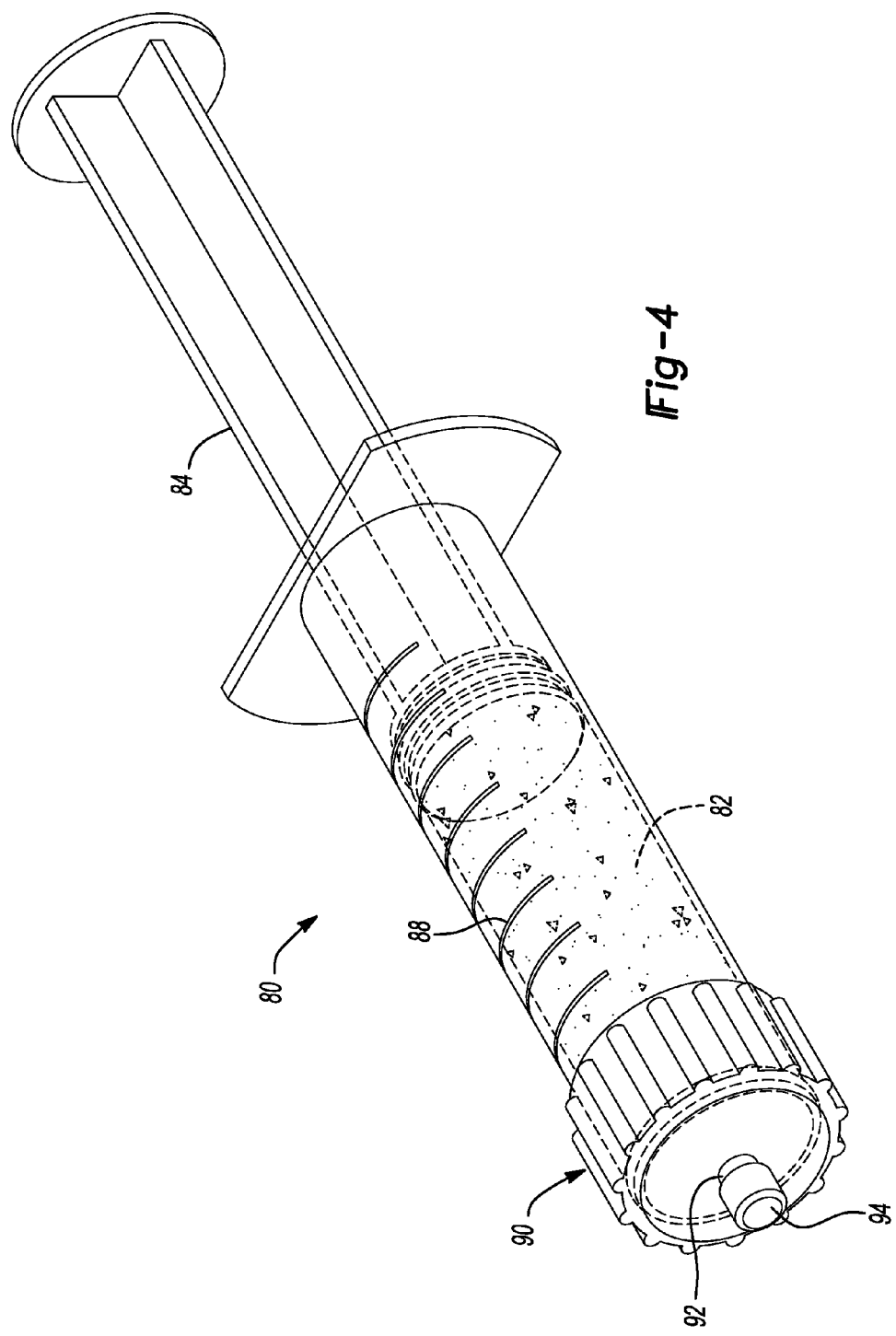
FIG. 4 is a diagrammatic illustration of a delivery syringe containing bone graft material, wherein the delivery syringe is coupled to a filter assembly.

As depicted in FIG. 3, the present technology provides a method 60 for rinsing and delivering a bone graft. In block 62 of the method 60, a delivery syringe containing bone graft material and cryopreservation solution is selected. Preferably, the delivery syringe containing the bone graft material was in storage at −80° C. The delivery syringe can be substantially similar to that depicted in FIG. 1. FIG. 4 shows a delivery syringe 80 with bone graft material 82 and cryopreservative solution contained therein. The delivery syringe 80 comprises a proximal plunger 84, a distal open bore 86, optional volumetric markings 88, and a filter assembly 90 removably coupled to the delivery syringe 80.

The filter assembly 90 comprises a nozzle opening 92 with a detachable cap 94, and a filter (as depicted in FIG. 2). The bone graft material 82 comprises bone particles. The bone particles have diameters of from about 50 µm to about 5 mm. Preferably, the bone particles have diameters of from about 100 µm to about 4 mm. As described previously, the filter 50 has a pore size that can be smaller than the diameter of the smallest bone particles of the graft material 82. Therefore, if the smallest bone particle has a diameter of, for example, about 60 µm, the filter 50 will have a pore diameter that is smaller than 60 µm. In some embodiments, bone particles with negligible size, such as bone particles with a diameter of about 40 µm or less, can pass through the filter 50. Bone dust and bone particle are examples of bone particles that have negligible size. Therefore, according to various embodiments, the pores have a diameter of from about 2 µm to about 250 µm, or from about 2 µm to about 200 µm, or from about 2 µm to about 150 µm, or from about 2 µm to about 100 µm, or from about 2 µm to about 50 µm. Preferably, the pores have a diameter of from about 150 µm to about 200 µm.

In a preferred embodiment, the pores have a diameter of about 185 µm and the bone particles have a diameter of from about 125 µm to about 4000 µm. Because a small fraction of bone particles have a diameter that is smaller than the diameter of the pores, a small amount of the bone particles may pass through the filter 50. However, because the amount of bone particles that has a diameter of from about 125 µm to about 185 µm is extremely small relative to the total amount of bone particles, the amount of bone particles that can pass through the filter 50 is negligible. Therefore, bone particles, such as bone dust and bone powder, that have diameters smaller than about 185 µm, are considered to be of negligible size. Furthermore, not all bone particles with a diameter smaller than about 185 µm will pass through the filter 50. Many small bone particles with diameters smaller than about 185 µm will become entangled between larger particles, which can trap them at a distance away from the filter 50. These small bone particles may never pass through the filter 50.

Referring back to FIG. 3, in block 64, a bone graft:fluid ratio is determined. The bone graft:fluid ratio can be determined by a suitable person, such as a medical doctor, a skilled medical technician, or other person with ordinary skill in the art. Applications that require a course, thick bone graft will necessitate a high bone graft:fluid ratio and applications that require a wet, thin bone graft will necessitate a low bone graft:fluid ratio. For example, a bone graft:fluid ratio of 10:1 will result in a course, thick bone graft. On the other hand, a bone graft:fluid ratio of 1:1 will result in a runny, thin bone graft. Therefore, the bone graft:fluid ratio can be from about 1:10 to about 1:1. Specifically, the bone graft:fluid ratio can be about 10:1, about 9:1, about 8:1, about 7:1, about 6:1, about 5:1, about 4:1, about 3:1, about 2:1, or about 1:1. In some embodiments, the bone graft will not contain any additional reconstitution fluid. A bone graft that does not contain any reconstitution fluid will have a bone graft:fluid ratio of 1:0. Such a bone graft is referred to as "hydrated."

In block 66, the plunger 84 is depressed, which expels the cryopreservative solution through the open bore 86, through the filter contained within the filter assembly 90 and out the nozzle opening 92. The nozzle cap 94 must first be removed before depressing the plunger 84. Because the filter has a pore size smaller than the bone particles of the graft material 82, the graft material 82 remains within the delivery syringe

80. Due to the large surface area of the filter, the filter is not clogged by the graft material 82.

In block 68, the bone graft material 82 is washed. Washing is performed by inserting the nozzle opening 92 of the filter assembly 90 into a wash solution contained within a receptacle. The plunger 84 is drawn to aspirate the wash solution into the delivery syringe 80. In some embodiments, a flexible conduit is attached to the nozzle opening 92 to facilitate aspiration of the wash solution into the delivery syringe 80. The delivery syringe 80 is then inverted from 1 to 10 times to mix the bone graft material 82 with the wash solution. Preferably, the delivery syringe 80 is inverted 5 times. The plunger 84 is then depressed to expel the wash solution out of the delivery syringe 80. If a flexible conduit was used during the aspiration, it can be removed when expelling the wash solution out of the delivery syringe 80. The washing process is performed from 1 to 5 times. Preferably, block 68 comprises 3 washes. For example, after block 68 has been performed once, it can be repeated two more times. Preferred wash solutions include saline and phosphate buffered saline (PBS). Washing both removes the cryopreservative from the bone graft material and hydrates the bone graft material. In some embodiments, such as where the predetermined bone graft:fluid ratio is 1:0, the bone graft material can be administered to a surgical site after block 68.

In block 70, the bone graft material 82 is reconstituted in reconstitution fluid to obtain the predetermined bone graft: fluid ratio. Reconstituting is performed by inserting the nozzle opening 92 of the filter assembly 90 into reconstitution fluid contained within a second receptacle. The plunger 84 is drawn to aspirate the reconstitution fluid into the delivery syringe 80. Again, in some embodiments, a flexible conduit is attached to the nozzle opening 92 to facilitate aspiration of the reconstitution fluid into the delivery syringe 80. In one embodiment, a precise amount of reconstitution fluid is aspirated into the delivery syringe 80 to obtain the predetermined bone graft:fluid ratio. For example, if the delivery syringe 80 contains 5 cc of bone graft material 82 and a bone graft:fluid ratio of 5:1 was determined in block 64, then 1 cc of reconstitution fluid should be drawn into the delivery syringe. The volumetric markings 88 on the delivery syringe 80 can be used to determine when a sufficient amount of reconstitution fluid has been aspirated. If the space between the markings denote 1 cc, and the delivery syringe 80 contains 5 cc of bone graft material 82 based on the volumetric markings 88 after block 68, then the plunger 84 should be drawn until the contents of the delivery syringe 80 reaches a 6 cc marking due to the addition of reconstitution fluid. Where the volumetric markings 88 represent equal but arbitrary units of volume, then the user can determine how much reconstitution fluid to add based on the amount of bone graft material 82 in the delivery syringe 80 after the wash of block 68. For example, if the delivery syringe 80 contains bone graft material to a third marking after block 68, and a bone graft:fluid ratio of 1:1 was determined in block 64, then the plunger 84 should be drawn until the contents of the delivery syringe 80 reaches a $6^{th}$ marking due to the addition of reconstitution fluid. When the predetermined bone graft:fluid ratio is obtained, the delivery syringe 80 is inverted from 1 to 10 times to mix the bone graft material 82 with the reconstitution fluid to generate a bone graft. Preferably, the delivery syringe is inverted 5 times.

In another embodiment, an excess amount of reconstitution fluid is aspirated into the delivery syringe 80 by drawing the plunger 84. The plunger 84 is then depressed to adjust bone graft:fluid ratio. For example, if the delivery syringe 80 contains 5 cc of bone graft material 82 based on the volumetric markings 88 after the wash of block 68, and a bone graft:fluid ratio of 5:1 was determined in block 64, then an excess of 1 cc of reconstitution fluid can be aspirated into the delivery syringe 80. The plunger 84 is then depressed to expel excess reconstitution fluid from the nozzle opening 92 until the contents of the delivery syringe 80 reaches the 6 cc marking to obtain the predetermined 5:1 bone graft:fluid ratio. When the predetermined bone graft:fluid ratio is obtained, the delivery syringe 80 is inverted from 1 to 10 times to mix the bone graft material 82 with the reconstitution fluid to generate a bone graft. Preferably, the delivery syringe 80 is inverted 5 times.

Because the bone graft material comprises living cells, the reconstitution fluid should provide the desired fluidity of the bone graft material as well as provide a suitable environment and nutrients for bone growth. Therefore, reconstitution fluid is selected from the group of fluids consisting of saline, PBS, whole blood, a blood fraction, bone marrow aspirate, concentrated bone marrow aspirate, and combinations thereof. A blood fraction can be white blood cells, platelets, platelet rich plasma, platelet poor plasma, or combinations thereof. White blood cells include monocytes, lymphocytes, granulocytes, and combinations thereof. Granulocytes include neutrophils, eosinophils, basophils, and combinations thereof.

In various embodiments, the reconstitution fluid further comprises a supplemental component. The supplemental component can promote growth from the bone graft material or help prevent or decrease inflammation. Non-limiting examples of supplemental components include interleukin-1 receptor antagonist (IL-1ra), soluble tumor necrosis factor-receptor I (sTNF-RI), soluble tumor necrosis factor-receptor II (sTNF-RII), soluble interleukin-1 receptor II (sIL-1 RID, platelet-derived growth factor-AB (PDGF-AB), platelet-derived growth factor-BB (PDGF-BB), insulin-like growth factor-I (IGF-I), transforming growth factor-β1 (TGF-β1), hepatocyte growth factor (HGF), vascular endothelial growth factor (VEGF), epidermal growth factor (EGF), and combinations thereof. The supplemental component can be isolated form autologous tissue, isolated form allogeneic tissue, isolated from xenographic tissue, or it can be purified recombinant protein. The supplemental component may also be a suspension of cells, such as stromal cells or mesenchymal stem cells.

In some embodiments, the reconstitution fluid comprises an antimicrobial component. Suitable antimicrobial agents may have at least one or more of the following properties: 1) the ability to prevent growth and/or replication and/or to kill pathogens which become associated with the bone graft material through their ability to bind to blood, muscle and osseous tissue; 2) possessing an acceptable side effect profile, including low toxicity and allergenicity for the intended human or animal subject to be treated; 3) acceptable efficacy at the surgical site, with limited development of microbial resistance; 4) acceptable miscibility or solubility with the reconstitution fluid; and 5) stability over a period of time after the method 60 is performed. In various embodiments, the antimicrobial component is an antibiotic. The amount of antimicrobial agent in the reconstitution fluid may range from about 0.1% to about 20%, from about 1% to about 15%, from about 1% to about 10%, or from about 1% to about 5%.

Antibiotics useful herein include, for example, rifamycins, fosfobycin, fusidic acid, glycylcyclines, aminoglycosides, quinolones, glycopeptides, bismuth thiols, sulfonamides, trimethoprim, macrolides, oxazolidinones, β-lactams, lincosamides, chloramphenicol, gramicidins, polymyxins, lipodepsipeptides, bacitracins, tetracyclines, penicillin, ampicillin, cefazolin, clindamycin, erythromycins, levofloxacin, vancomycin, and mixtures thereof. In various embodiments, the anti-infective comprises rifampin and a second anti-infective, such as a combination of rifampin and a minocycline.

Tetracycline antibiotics refer to a number of antibiotics of either natural, or semi-synthetic origin, derived from a system of four linearly annealed six-membered rings (1,4, 4a,5,5a,6,11,12a-octahydronaphthacene) with a characteristic arrangement of double bonds. The tetracycline antibiotic can include one or more tetracyclines, and/or semi-synthetic tetracyclines such as doxycycline, oxytetracycline, demeclocycline, lymecycline, chlortetracycline, tigecycline and minocycline. A preferred tetracycline is minocycline or minocycline hydrochloride. The amount of tetracycline present in the reconstitution fluid can range from about 5 $\mu g/cm^2$ to about 1000 $\mu g/cm^2$, or from about 10 $\mu g/cm^2$ to about 800 $\mu g/cm^2$.

Rifamycin class of antibiotics is a subclass of antibiotics from the ansamycin family of antibiotics. The present antibiotic agent or agents can include one or more rifamycin antibiotics from the group rifamycin B, rifampin or rifampicin, rifabutin, rifapentine and rifaximin. Rifampin is commercially available as Rifadin and Rimactane from Sanofi-Aventis U.S. LLC. (Bridgewater, N.J., USA).

In some embodiments, the antimicrobial component is an antimicrobial peptide. Antimicrobial peptides useful herein include, for example, host defense proteins, defensins, magainins, cathetlicidins, protegrins, lantibiotics, nisins, and synthetic mimics of host defense proteins such as cationic steroids. Antiseptics and disinfectants include, for example, chlorhexidine, polyhexanide, triclosan, and iodine-delivering formulas such as betadine or povidone-iodine. Metal ions include various formulations of silver that effectively release silver ions, including silver salts and silver nanoparticles, or copper salts and copper nanoparticles that release copper ions.

Figure 5:
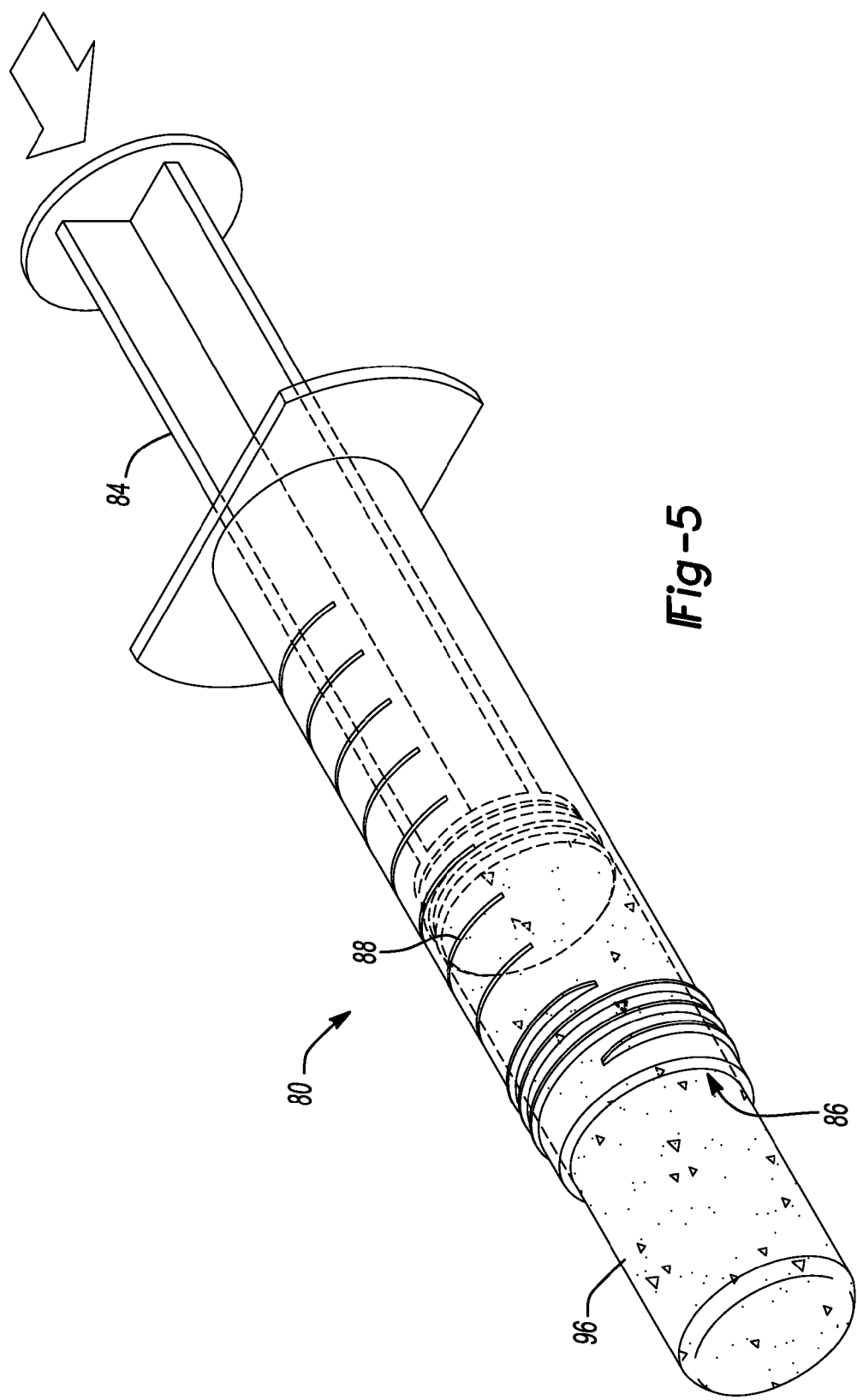
FIG. 5 is a diagrammatic illustration of a delivery syringe, wherein the plunger is being depressed to deliver a bone graft.

With reference to FIGS. 3 and 5, in block 72 the reconstituted bone graft 96 is delivered to a surgical site. Delivering the bone graft 96 comprises removing or decoupling the filter assembler 90 from the delivery syringe 80. Because in FIG. 5 the filter assembly 90 is coupled to the delivery syringe 80 by complimentary threading, the filter assembly 90 can be unscrewed from the delivery syringe 80. After the filter assembly 90 has been removed, the now exposed open bore 86 is positioned adjacent to the surgical site. As shown in FIG. 5, depressing the plunger causes the bone graft 96 to be delivered from the delivery syringe 80. The delivery site can be on a human or non-human animal. Non-human animals include dogs, cats, horses, and other animals that can benefit from receiving a bone graft.

Embodiments of the present technology are further illustrated through the following non-limiting examples.

Example 1

Rinsing and Delivering a Bone Graft Reconstituted in PBS

A delivery syringe containing bone graft material and a cryopreservative solution is selected from a −80° C. freezer. The delivery syringe comprises a proximal plunger, a distal open bore, volumetric markings, and a filter assembly removably coupled to the delivery syringe adjacent to the distal open bore. The filter assembly comprises a nozzle opening with a detachable cap, and a filter. Based on the surgical site and the desired fluidity of the graft material desired, a bone graft:phosphate buffered saline (PBS) ratio of 5:1 is determined. The detachable cap is removed and the plunger is depressed to expel the cryopreservative solution from the delivery syringe and into a waste container. Because the graft material is larger than the pore size of the filter in the filter assembly, the graft material remains within the delivery syringe.

The bone graft material is washed three times by inserting the nozzle opening of the filter assembly into a saline solution. The plunger is drawn to aspirate the saline solution into the delivery syringe. The delivery syringe is then inverted 5 times to mix the bone graft material with the saline solution. The plunger is then depressed to expel the saline solution out of the delivery syringe. The volume of the bone graft material is noted from the volumetric markings on the delivery syringe.

The bone graft material is reconstituted in phosphate buffered saline by inserting the nozzle opening of the filter assembly into the phosphate buffered saline. The plunger is drawn to aspirate the phosphate buffered saline until the 5:1 bone graft:PBS ratio is obtained with reference to the volumetric markings. The delivery syringe is inverted 5 times to mix the bone graft material with the PBS to generate the bone graft. The filter assembly is detached from the delivery syringe and the plunger is depressed to deliver the bone graft to a surgical site.

Example 2

Rinsing and Delivering a Bone Graft Reconstituted in Bone Marrow Aspirate

A delivery syringe containing bone graft material and a cryopreservative solution is selected from a −80° C. freezer. The delivery syringe comprises a proximal plunger, a distal open bore, volumetric markings, and a filter assembly removably coupled to the delivery syringe adjacent to the distal open bore. The filter assembly comprises a nozzle opening with a detachable cap, and a filter. Based on the surgical site and the desired fluidity of the graft material desired, a bone graft:bone marrow aspirate ratio of 3:1 is determined. The detachable cap is removed and the plunger is depressed to expel the cryopreservative solution form the delivery syringe and into a waste container. Because the graft material is larger than the pore size of the filter in the filter assembly, the graft material remains within the delivery syringe.

The bone graft material is washed three times by inserting the nozzle opening of the filter assembly into PBS. The plunger is drawn to aspirate the PBS into the delivery syringe. The delivery syringe is then inverted 5 times to mix the bone graft material with the PBS. The plunger is then depressed to expel the PBS out of the delivery syringe. The volume of the bone graft material is noted from the volumetric markings on the delivery syringe.

The bone graft material is reconstituted in bone marrow aspirate by inserting the nozzle opening of the filter assembly into the bone marrow aspirate. The plunger is drawn to aspirate an excess amount of the bone marrow aspirate. The plunger is then slowly depressed until the 3:1 bone graft:bone marrow aspirate ratio is obtained with reference to the volumetric markings. The delivery syringe is inverted 5 times to mix the bone graft material with the bone marrow aspirate to generate the bone graft. The filter assembly is detached from the delivery syringe and the plunger is depressed to deliver the bone graft to a surgical site.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A method for rinsing and delivering a bone graft comprising:
   a. selecting a delivery syringe comprising a proximal plunger, a distal open bore, and a filter assembly comprising a filter and a nozzle, the filter being removably coupled to the syringe adjacent to the distal open bore, and the syringe having a bone graft material and a cryopreservative solution therein;
   b. determining a bone graft material:fluid ratio;
   c. depressing the plunger to expel the cryopreservative solution from the delivery syringe, through the filter and out the nozzle, wherein the bone graft material is maintained within the syringe;
   d. inserting a distal end of the syringe into a receptacle containing a wash solution and drawing the plunger to aspirate a wash solution into the syringe;
   e. inverting the syringe to mix the wash solution with the bone graft material;
   f. depressing the plunger to expel the wash solution;
   g. d. through f. to wash the bone graft material;
   h. reconstituting the bone graft material, including inserting the distal end of the syringe into a second receptacle containing a reconstitution fluid and drawing the plunger to aspirate the reconstitution fluid to generate the bone graft with the predetermined bone graft material:fluid ratio; and
   i. removing the filter assembly from the syringe and delivering the bone graft material through the open bore to a surgical site by depressing the plunger.

2. The method according to claim 1, wherein d. through f. are repeated one or more times.

3. The method according to claim 1, wherein the wash solution comprises saline or phosphate buffered saline.

4. The method according to claim 1, wherein the reconstitution fluid is selected from saline, phosphate buffered saline, whole blood, a blood fraction, bone marrow aspirate, concentrated bone marrow aspirate, and a combination thereof.

5. The method according to claim 1, wherein the reconstitution fluid comprises monocytes, lymphocytes, neutrophils, eosinophils, basophils, platelets, platelet rich plasma, platelet poor plasma, or a combination thereof.

6. The method according to claim 1, wherein the reconstitution fluid comprises stromal cells, mesenchymal stem cells, or both.

7. The method according to claim 1, wherein reconstituting includes inverting the syringe to mix the bone graft material and the reconstitution fluid.

8. The method according to claim 1, wherein the reconstitution fluid comprises a supplemental component that is autologous to the subject.

9. The method according to claim 1, wherein the reconstitution fluid comprises a component selected from interleukin-1 receptor antagonist (IL-1ra), soluble tumor necrosis factor-receptor I (sTNF-RI), soluble tumor necrosis factor-receptor II (sTNF-RII), soluble interleukin-1 receptor II (sIl-1 RII), platelet-derived growth factor-AB (PDGF-AB), platelet-derived growth factor-BB (PDGF-BB), insulin-like growth factor-I (IGF-I), transforming growth factor-$\beta1$ (TGF-$\beta1$), hepatocyte growth factor (HGF), vascular endothelial growth factor (VEGF), epidermal growth factor (EGF), and a combination thereof.

10. The method according to claim 1, wherein the bone graft material:fluid ratio is from about 10:1 to about 1:1.

11. The method according to claim 1, wherein reconstituting includes aspirating an excess amount of the reconstitution fluid into the syringe and depressing the plunger to expel a portion of the reconstitution fluid out through the filter until the predetermined bone graft material:fluid ratio is obtained.

12. A method comprising:
    obtaining a syringe comprising a filter removably coupled to the syringe, wherein the syringe has bone graft particles and a cryopreservative solution contained therein, and wherein the filter has a pore size such that only a negligible amount of the bone graft particles can pass through;
    depressing a plunger of the syringe to expel the cryopreservative solution through the filter, wherein the bone graft particles are maintained within the syringe;
    washing the bone graft particles, including drawing the plunger to aspirate a wash solution into the syringe, inverting the syringe to mix the wash solution and bone graft particles, and depressing the plunger to expel the wash solution;
    reconstituting the bone graft particles in a reconstitution fluid;
    removing the filter from the syringe; and
    depressing the plunger to deliver the bone graft particles through an open bore of the syringe.

13. The method according to claim 12, wherein the wash solution is different from the reconstitution fluid.

14. The method according to claim 12, wherein the wash solution comprises saline or phosphate buffered saline.

15. The method according to claim 12, wherein reconstituting the graft material comprises:
    drawing the plunger to aspirate an excess amount of the reconstitution fluid;
    inverting the syringe to mix the reconstitution fluid with the bone graft particles; and
    depressing the plunger to expel a portion of the reconstitution fluid until a desired bone graft particle:fluid ratio is obtained.

16. The method according to claim 12, wherein the reconstitution fluid comprises saline, phosphate buffered saline, an antimicrobial agent, whole blood, a blood fraction, bone marrow aspirate, concentrated bone marrow aspirate, or a combination thereof.

17. The method according to claim 12, wherein the reconstitution fluid comprises stromal cells or mesenchymal stem cells.

18. The method according to claim 12, wherein the filter has a pore size between about 150 µm and about 200 µm.

19. The method according to claim 12, wherein the bone graft particles have diameters ranging from about 125 µm to about 5000 µm.

20. A method for rinsing and delivering a bone graft comprising:
    a. selecting a syringe containing bone graft material and a cryopreservative solution, the syringe comprising a proximal plunger, a distal open bore, and a filter removably coupled to the syringe adjacent to the distal open bore, wherein the bone graft material comprises bone particles with diameters of from about 50 µm to about 5 mm and wherein the filter has a pore size of from about 150 µm to about 200 µm;

b. determining a bone graft material:fluid ratio of from about 10:1 to about 1:1;

c. depressing the plunger to expel the cryopreservative solution from the syringe and through the filter, wherein the bone graft material is maintained within the syringe;

d. inserting a distal end of the syringe into a receptacle containing a wash fluid and drawing the plunger to aspirate the wash solution into the syringe, wherein the wash fluid is saline or phosphate buffered saline;

e. inverting the syringe to mix the wash solution with the bone graft material;

f. depressing the plunger to expel the wash solution;

g. repeating d. through f. one or more times to wash the bone graft material;

h. reconstituting the bone graft material by inserting the distal end of the syringe into a second receptacle containing a reconstitution fluid and drawing the plunger to aspirate the reconstitution fluid to obtain the bone graft material with the predetermined bone graft material:fluid ratio, wherein the reconstitution fluid comprises saline, phosphate buffered saline, whole blood, white blood cells, platelets, platelet rich plasma, platelet poor plasma, bone marrow aspirate, concentrated bone marrow aspirate, or a combination thereof; and i. removing the filter from the syringe and delivering the reconstituted bone graft material through the open bore to a surgical site by depressing the plunger.

* * * * *